United States Patent
Lynch et al.

(10) Patent No.: US 12,186,585 B2
(45) Date of Patent: Jan. 7, 2025

(54) QUANTUM COMPUTATION FOR INTENSITY-MODULATED RADIATION THERAPY

(71) Applicant: Accenture Global Solutions Limited, Dublin (IE)

(72) Inventors: Cecil Lynch, Granite Bay, CA (US); Kung-Chuan Hsu, Cerritos, CA (US); Shreyas Ramesh, Mountainside, NJ (US); Carl Matthew Dukatz, Troy, MI (US); Felix Dominik Schiessl, Hattersheim (DE); Tim Leonhardt, Munich (DE); Max Howard, San Francisco, CA (US)

(73) Assignee: Accenture Global Solutions Limited, Dublin (IE)

(*) Notice: Subject to any disclaimer, the term of this patent is extended or adjusted under 35 U.S.C. 154(b) by 959 days.

(21) Appl. No.: 17/212,815

(22) Filed: Mar. 25, 2021

(65) Prior Publication Data

US 2021/0316157 A1    Oct. 14, 2021

Related U.S. Application Data

(60) Provisional application No. 63/007,666, filed on Apr. 9, 2020.

(51) Int. Cl.
*A61N 5/10* (2006.01)
*G05B 19/4155* (2006.01)
(Continued)

(52) U.S. Cl.
CPC ....... *A61N 5/1031* (2013.01); *G05B 19/4155* (2013.01); *G06F 16/2425* (2019.01);
(Continued)

(58) Field of Classification Search
CPC ................ A61N 5/1031; A61N 5/1045; G05B 19/4155; G05B 2219/45117;
(Continued)

(56) References Cited

U.S. PATENT DOCUMENTS 10,031,887 B2    7/2018    Raymond

OTHER PUBLICATIONS

Nazareth et al., "First application of quantum annealing to IMRT beamlet intensity optimization," Phys. Med. Biol . . . May 2015, 60: 4137, 13 pages (Year: 2015).*

(Continued)

*Primary Examiner* — Thaddeus B Cox
*Assistant Examiner* — Joshua Daryl D Lannu
(74) *Attorney, Agent, or Firm* — Polsinelli PC

(57) ABSTRACT

Methods, systems, and apparatus for generating intensity modulated radiation therapy treatment plans. In one aspect, a method includes receiving data representing an optimization problem; iteratively processing, until termination criteria are met, the received data representing the optimization problem to obtain data representing a solution to the optimization problem, comprising, for each iteration: performing a classical search algorithm on an input for the iteration to determine a first solution; providing data representing the first solution to a quantum computing resource, wherein the data representing the first solution comprises a quadratic unconstrained binary optimization formulation of the optimization problem in a local region around the first solution; obtaining data representing a second solution from the quantum computing resource; and providing the data representing the second solution as input to a subsequent iteration; and initiating an action based on the data representing a solution to the optimization problem.

18 Claims, 9 Drawing Sheets

(51) Int. Cl.
  *G06F 16/242* (2019.01)
  *G06F 17/11* (2006.01)
  *G06N 5/01* (2023.01)
  *G06N 10/00* (2022.01)
  *G06N 10/60* (2022.01)
  *G16H 20/40* (2018.01)
  *G16H 40/40* (2018.01)
  *G16H 50/20* (2018.01)
  *G16H 50/30* (2018.01)
  *G16H 50/70* (2018.01)

(52) U.S. Cl.
  CPC .............. *G06F 17/11* (2013.01); *G06N 10/00* (2019.01); *G06N 10/60* (2022.01); *G16H 20/40* (2018.01); *G16H 40/40* (2018.01); *G16H 50/20* (2018.01); *G16H 50/30* (2018.01); *G16H 50/70* (2018.01); *A61N 5/1045* (2013.01); *G05B 2219/45117* (2013.01)

(58) Field of Classification Search
  CPC ..... G06F 16/2425; G06F 17/11; G06N 10/00; G06N 10/60; G06N 5/01; G16H 20/40; G16H 40/40; G16H 50/20; G16H 50/30; G16H 50/70
  See application file for complete search history.

(56) References Cited

OTHER PUBLICATIONS

Booth et al., "Partitioning Optimization Problems for Hybrid Classical/Quantum Execution: Technical Report," D-Wave Technical Report Series, Jan. 9, 2017, 13 pages.

EP Extended Search Report in European Appln. No. 21165355.5, dated Sep. 9, 2021, 11 pages.

Malekmohammadi et al., "A Hamiltonian Engine for Radiotherapy Optimization," Thesis for the degree of Master of Applied Science, University of Toronto, Graduate Department of Electrical and Computer Engineering, 2019, 89 pages.

Nazareth et al., "First application of quantum annealing to IMRT beamlet intensity optimization," Phys. Med. Biol., May 2015, 60:4137, 13 pages.

* cited by examiner

QUANTUM COMPUTATION FOR INTENSITY-MODULATED RADIATION THERAPY

CROSS-REFERENCE TO RELATED APPLICATION

This application claims the benefit of U.S. Provisional Application No. 63/007,666, filed Apr. 9, 2020, and titled "Quantum Computation for Intensity-Modulated Radiation Therapy," which is incorporated by reference.

TECHNICAL FIELD

The present invention relates to quantum computing.

BACKGROUND

External Beam Radiotherapy requires the development of successive radiation treatment plans. These treatment plans need to be calculated regularly, e.g., daily, as tumors respond to the treatment. These treatment plans are therefore time sensitive. Computational methods for producing high quality treatment plans typically require solving combinatorial optimization problems with many variables, e.g., radiation intensity, beamlet angles, radiation sequence, and those resulting from complex modelling of 3-dimensional body tissue imaging, which produces a massive search space. Resource scarcity means a low percentage of patients receive highest quality computational radiation plans.

SUMMARY

This specification describes methods and systems for solving optimization problems using quantum computing resources.

In general, one innovative aspect of the subject matter described in this specification can be implemented in a method for solving an optimization problem, the method including receiving data representing an optimization problem; iteratively processing, until termination criteria are met, the received data representing the optimization problem to obtain data representing a solution to the optimization problem, comprising, for each iteration: performing a classical search algorithm on an input for the iteration to determine a first solution to the optimization problem; providing data representing the first solution to the optimization problem to a quantum computing resource, wherein the data representing the first solution to the optimization problem comprises a quadratic unconstrained binary optimization (QUBO) formulation of the optimization problem in a local region around the first solution to the optimization problem; obtaining data representing a second solution to the optimization problem from the quantum computing resource; and providing the data representing the second solution to the optimization problem as input to a subsequent iteration; receiving solution data from the processing; and initiating an action based on the solution data.

Other implementations of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations the optimization problem comprises an objective function to be optimized over multiple problem parameters.

In some implementations the local region around the first solution to the optimization problem comprises multiple discretized values of the multiple problem parameters, wherein: each discretized value comprises a respective binary sequence, and a Hamming distance between each discretized value and a binary sequence representation of the first solution is at most 2.

In some implementations the method further comprises generating the quadratic unconstrained binary optimization (QUBO) formulation of the optimization problem in a local region around the first solution to the optimization problem, comprising: selecting a discretization for the optimization problem; applying the discretization to the optimization problem to obtain discretized values of the multiple problem parameters, wherein each discretized value comprises a respective binary sequence; and determining a binary sequence corresponding to a discretization of the first solution to the optimization task.

In some implementations selecting the discretization for the optimization problem comprises selecting a normalization factor to position the discretization of the first solution to the optimization task in a centre of a corresponding discretization interval.

In some implementations generating the quadratic unconstrained binary optimization (QUBO) formulation of the optimization problem in a local region around the first solution to the optimization problem further comprises: determining a set of second bit sequences, wherein a Hamming distance of a first bit sequence representing the first solution and each second bit sequence is at most 2; generating a system of equations, comprising, for each second bit sequence in the set of second bit sequences: determining a product of i) a transposed vector form of the second bit sequence, ii) a matrix representing total radiation dose, and iii) a vector form of the second bit sequence; and setting the determine product as equal to an objective function for the optimization problem evaluated at the second bit sequence; and solving the system of equations to determine entries of the matrix representing total radiation dose.

In some implementations the matrix comprises an upper triangular matrix.

In some implementations the first bit sequence and each second bit sequence have a length equal to a number of optimization problem parameters.

In some implementations the generated system of equations comprises $$\frac{N_B(N_B + 1)}{2}$$

equations, wherein $N_B$ represents a number of optimization problem parameters.

In some implementations the QUBO formulation of the optimization problem in a local region around the first solution to the optimization problem comprises a scaled Hamming penalty.

In some implementations the QUBO formulation of the optimization problem in a local region around the first solution to the optimization problem comprises a scaled quadratic Hamming penalty.

In some implementations the optimization problem comprises an intensity-modulated radiation therapy (IMRT) treatment problem.

In some implementations the IMRT treatment problem comprises an objective function to be minimized, wherein the objective function comprises a linear combination of two terms, a first term representing differences between i) a minimal amount of radiation dose to be received by a target body structure and ii) a smallest dose a volume of the target body structure receives, and a second term representing an amount that a minimal amount of radiation dose to be received by a body structure at risk exceeds a smallest dose a volume of the body structure at risk receives.

In some implementations the objective function is given by $$C(w) = \alpha \sum_{s \in S_{PTV}} (d_s - \tilde{D}_{s,v_s}(w))^2 + \sum_{s \in S_{OAR}} \beta_s \sum_{i=1}^{r_s} (\max\{0, \tilde{D}_{s,v_{s,i}}(w) - d_{s,i}\})^2$$

where $S_{PTV}$ represents a set of radiotherapy target body structures, $d_s$ represents a minimal amount of radiation dose to be received by structure s, $S_{OAR}$ represents a set of body structures that are at risk, $r_s$ represents a total number of dose-volume constraints for a structure s, $\alpha$ and $\beta_s$ are constants, $\tilde{D}_{s,v_s}(w)$ represents a smallest dose that $v_s$ of the volume of a respective body structure s is at least receiving, and w represents a vector of beamlet intensity weights where the i-th element $w_i$ of w represents a non-negative intensity weight of the i-th beamlet.

In some implementations the IMRT treatment problem comprises one or more dose-volume constraints, wherein each dose-volume constraint comprises a pair of values ($v_s$, $d_s$) that specify a minimal amount of radiation dose $d_s$ to be received by a total volume $v_s$ of a respective body structure s.

In some implementations the received data comprises patient specific data comprising a set of radiotherapy targets and a set of organs at risk.

In some implementations the solution to the optimization problem comprises a beamlet intensity setting for the IMRT treatment problem.

In some implementations initiating an action based on the obtained data representing a solution to the optimization problem comprises one or more of: programming a radiotherapy machine using the beamlet intensity setting, or operating the radiotherapy machine at the beamlet intensity setting.

The subject matter described in this specification can be implemented in particular ways so as to realize one or more of the following advantages.

This specification describes a formulation, process and web solution for solving complex optimization tasks, e.g., an IMRT beamlet intensity optimization treatment problem. The techniques leverage a hybrid quantum-classical method that enables a more efficient search of optimal solutions to the optimization problem. In particular, by reformulating an original optimization problem into a series of local search problems over approximate QUBO objectives, quantum computing resources can be used to perform better local optimizations that can produce accurate global optima.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
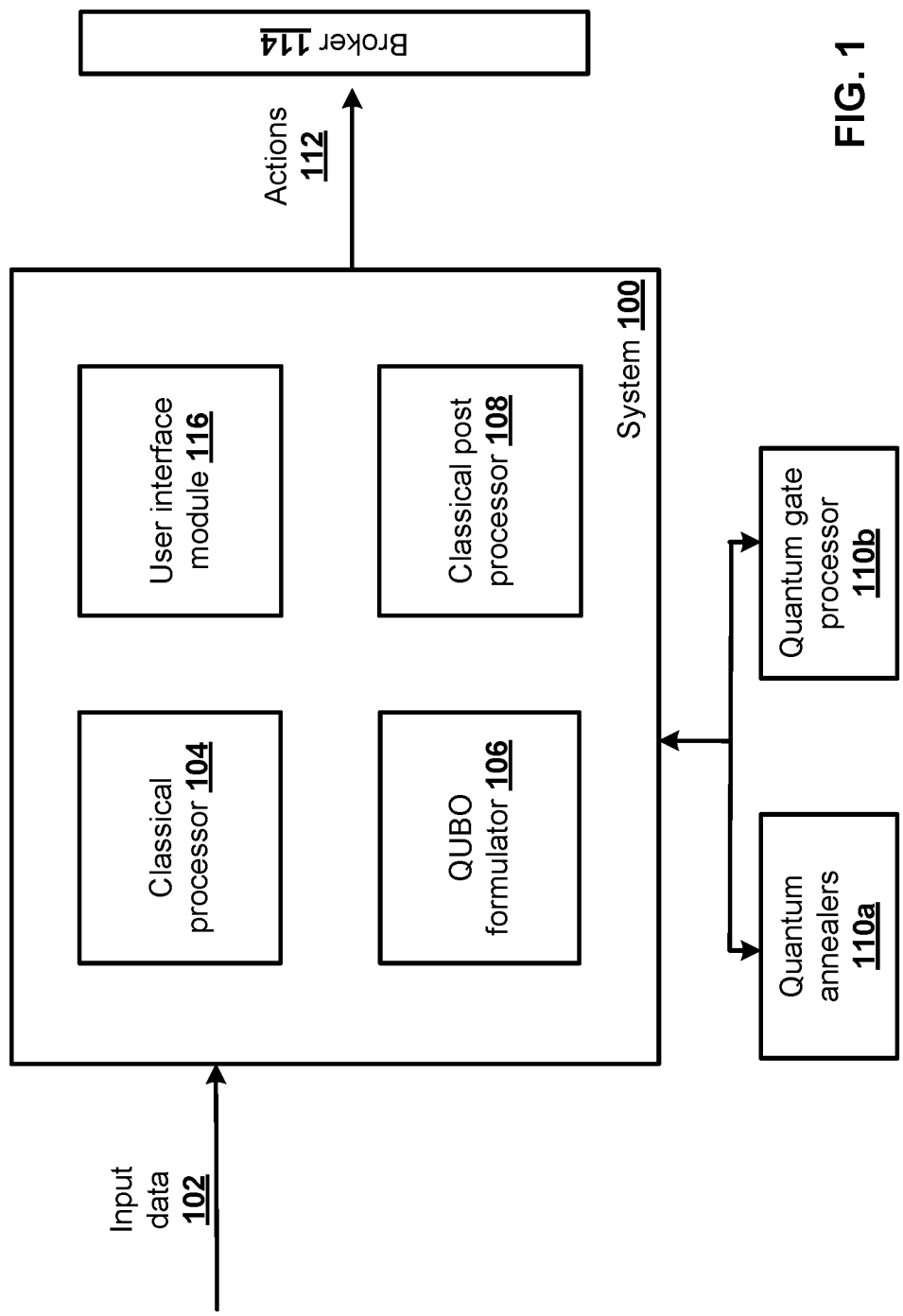
FIG. 1 shows an example system for obtaining a solution to an optimization problem.

FIG. 1 depicts an example system 100 for obtaining a solution to an optimization program. The system 100 is an example of a system implemented as computer program(s) on one or more classical or quantum computing devices in one or more locations, in which the systems, components, and techniques described below can be implemented.

The system 100 includes a classical processor 104, a QUBO formulator 106, a classical post-processor 108, and one or more quantum computing resources, e.g., quantum annealer 110a and quantum gate processor 110b. For convenience, two additional quantum computing resources are shown in FIG. 1, with the quantum computing resources being external to the system 100. However in some implementations the system 100 may be in communication with more or fewer additional quantum computing resources, or the system 100 may include the quantum computing resources. Components of the system 100 may be in data communication with each of the additional quantum computing resources, e.g., through a communication network such as a local area network or wide area network.

The system 100 is configured to receive as input data representing an optimization problem, e.g., input data 102. As described in more detail below with reference to step 202 of FIG. 2, the input data 102 may include data specifying an objective function to be minimized (or maximized) with respect to a set of parameters, and data representing constraints for the minimization (or optimization).

The system 100 processes the received input data 102 to generate as output data representing actions to be initiated, e.g., actions 112. The actions are based on a determined solution to the optimization problem. For example, the actions may include programming or operating a machine, e.g., a radiation machine, based on the solution to the optimization problem. In some implementations the solution to the optimization problem can be used to understand whether there could be an operation that would result in good quality or not. If the quality (based on the expected received dosage of different body tissues/organs computed using the solution) is tolerable, the solution could be fed into the radiation machine to operate on the patient. However, if the quality is not tolerable/acceptable, then this information could be sent back to the physician for further evaluation, e.g., to consider alternative or more advanced medication or radiation device.

The system 100 is configured to determine a solution to the optimization problem represented by the input data 102. To determine a solution to the optimization problem, the system 100 uses one or more of the classical processor 104, the QUBO formulator 106 or the classical post processor 108.

The classical processor 104 is configured to receive data inputs and to process the received data inputs using classical search algorithms to determine a first solution to the optimization task represented by the input data 102. For example the classical processor 104 may receive an initial input and subsequent inputs provided by the classical post processor 108 (which correspond to outputs generated by the quantum computing resources 110a, 110b.)

The classical processor 104 is configured to provide the determined first solutions to the QUBO formulator 106.

The QUBO formulator 106 is configured to receive the input data 102 and first solutions from the classical processor 104 and to generate data representing a QUBO formulation of the optimization problem in a local region around the first solution to the optimization problem. Example operations performed by the QUBO formulator 106 to generate such approximate QUBO objective functions are described below with reference to FIG. 2.

The system 100 is configured to transmit data representing generated QUBO formulations to one or more quantum computing resources. The quantum computing resources may include quantum annealer computing resources, e.g., quantum annealer 110a. A quantum annealer is a device configured to perform quantum annealing—a procedure for finding the global minimum of a given objective function over a given set of candidate states using quantum tunneling. Quantum tunneling is a quantum mechanical phenomenon where a quantum mechanical system overcomes localized barriers in the energy landscape which cannot be overcome by a classically described system. Some quantum annealer devices perform a subclass of quantum annealing called adiabatic quantum computing, which relies on the adiabatic theorem to perform computations.

Quantum annealer devices can solve problems if they are formulated in an acceptable format. For example, quantum annealer devices can solve some QUBO formulations of problems by mapping the QUBO formulation into a qubit network of a quantum annealer device.

The quantum computing resources may include one or more quantum gate processors, e.g., quantum gate processor 110b. A quantum gate processor includes one or more quantum circuits, i.e., models for quantum computation in which a computation is performed using a sequence of quantum logic gates, operating on a number of qubits (quantum bits).

Quantum gate processors can be used to solve certain optimization problems, e.g., problems that can be formulated as a QUBO problem. For example, some quantum gate processors can solve QUBO problems by simulating a corresponding adiabatic quantum annealing process using a gate model. This can be advantageous, e.g., compared to directly performing the corresponding adiabatic quantum annealing process using a quantum annealer device, since not all quantum annealer devices can realize physical quantum systems that represent an optimization problem. For example, some quantum annealer devices may not provide the physical interactions necessary to solve an optimization problem. In these examples, a Hamiltonian describing the optimization problem can be decomposed into a sequence of single or multi-qubit quantum gates, and a solution to the optimization problem can be obtained through application of the sequence of single or multi-qubit gates on a register of qubits and subsequent measurement of the register of qubits.

The one or more quantum computing resources that receive the transmitted data representing the QUBO formulations are configured to process the received data to generate output data 118 representing a second solution to the optimization problem. The one or more quantum computing resources are configured to provide the generated output data 118 to the system 100, e.g., to the classical post processor 108.

The system 100 is configured to receive the output data 118 from the one or more quantum computing resources. The classical post-processor 108 is configured to process the received output data 118. Processing the output data 118 may include determining whether termination criteria have been met or not, and determining one or more actions to be taken based on a solution to the optimization problem. Processing the output data 118 may also include generating a user interface presentation using the user interface module 116 based on the output data 118. Example user interface presentations generated by the user interface module 116 are shown in FIGS. 3-8.

The system 100 is configured to output data representing determined actions that can be taken 112. For example, the system 100 may provide the data 112 to, or include, a broker that initiates actions based on the output data.

Figure 2:
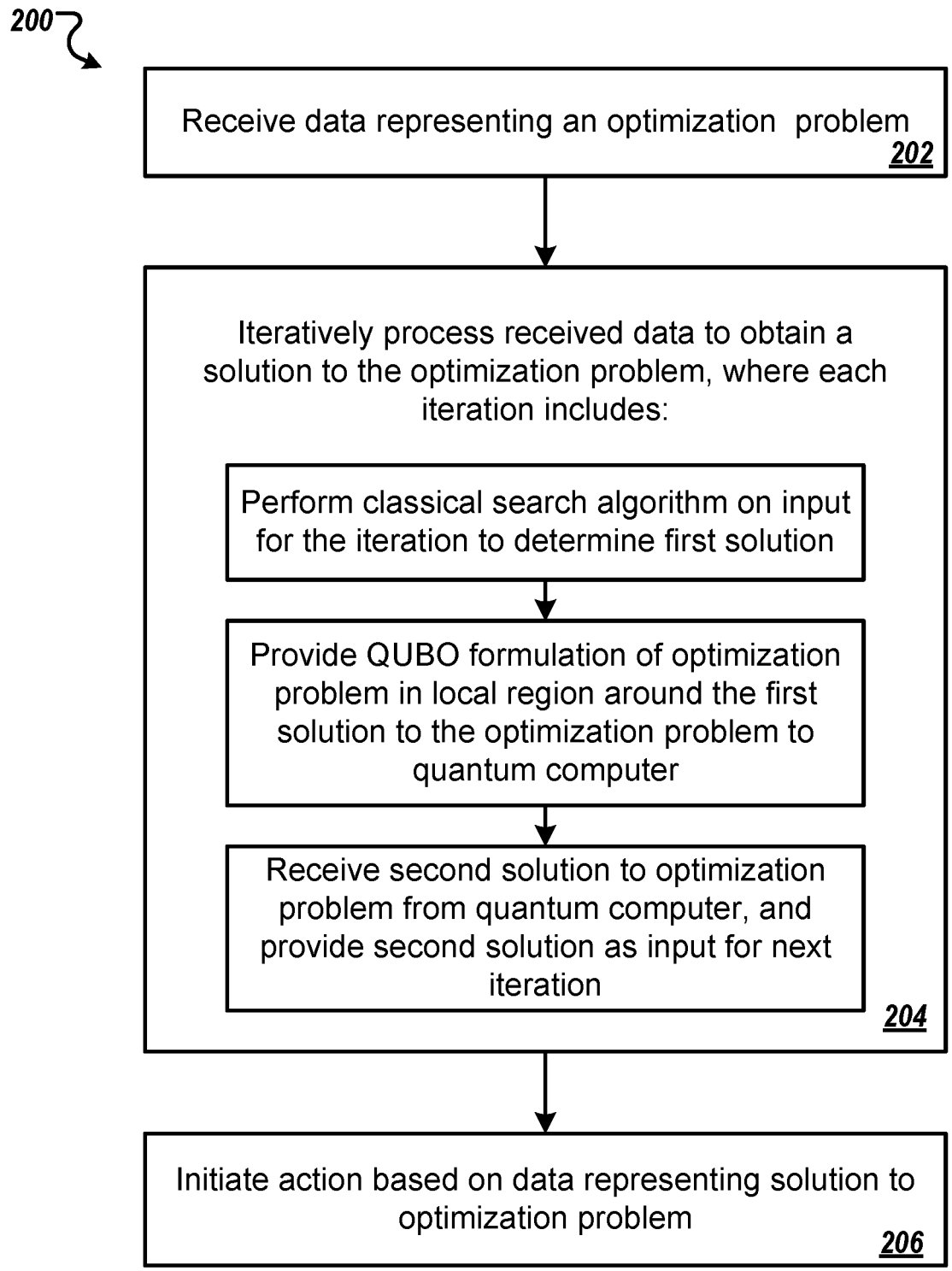
FIG. 2 is a flow diagram of an example process for solving an optimization problem using quantum computing resources.

FIG. 2 is a flowchart of an example process 200 for solving an optimization problem using quantum computing resources. For convenience, the process 200 will be described as being performed by a system of one or more classical or quantum computing devices located in one or more locations. For example, example system 100 of FIG. 1, appropriately programmed in accordance with this specification, can perform the process 200.

The system receives data representing the optimization problem (step 202). The received data may include data representing an objective function to be optimized over a given set of parameters. The received data may also include data representing one or more constraints, e.g., inequality or equality constraints.

In some implementations the optimization problem may be an intensity-modulated radiation therapy (IMRT) treatment problem, where the solution to the IMRT treatment problem is a beamlet intensity setting or a set of parameters (e.g., intensity settings) for a set of beamlets.

In these implementations the received data may be based on a IMRT beamlet model. The IMRT beamlet model can include a model for the volume of the operation, as described below.

Model for Volume

In the presently described techniques, the volume of the operation is modelled by the interior of a three-dimensional Cartesian grid. Without formally defining the grid, such as via definition of tessellation of geometrical space, a rectilinear grid can be considered as a set of rectangular cells piling next to each other to form a large rectangular volume. In the case that all rectangular cells are cubes, the grid is a Cartesian grid. In some implementations this could be extended to rectilinear grid or other more general relaxations of grid. The boundary of the set of cubes can be associated with the natural set of edges and square faces on the boundary, and the interior of the set of cubes can be associated with, in the natural topological sense, the union of the cubes but excluding the boundary.

Let the size of the grid be $D_1 \times D_2 \times D_3$, where $D_1, D_2, D_3 \in \mathbb{N}$, and let D represent the Cartesian product of the grid:

$$D = \{1, 2, \ldots, D_1\} \times \{1, 2, \ldots, D_2\} \times \{1, 2, \ldots, D_3\} =$$
$$\{(x, y, z) : x \in \{1, 2, \ldots, D_1\}, y \in \{1, 2, \ldots, D_2\}, z \in \{1, 2, \ldots, D_3\}\}$$

In this case, given a reference point, every cubic cell can be labeled by a unique Cartesian coordinate based on its position. Let S represent the set of all $D_1 \cdot D_2 \cdot D_3$ cubes, and let $$\eta: S \to \{1,2,\ldots,D_1\} \times \{1,2,\ldots,D_2\} \times \{1,2,\ldots,D_3\}$$

represent a 1-1 function assigning each cube with its coordinate in D. The cubes can be associated with their Cartesian coordinates, such that every $c \in D$ corresponds to a unique cube $\eta^{-1}(c) \in S$. The size of the cubes (the discretization) can vary—the model is general enough for any range of discretization. In some implementations a largest size of discretization can be the resolution of the medical image, e.g. a DICOM image which typically has a size between 256×256 to 512×512 pixels, with each pixel encoded by 16 bits. In some implementations the discretization can be approximately 10×20 pixels.

The IMRT beamlet model can also include a model for the body structure, as described below.

Model for Body Structure

A body structure is a physical structure that belongs to the body of a patient. It is a geometrical object that can be of any shape. Given the grid volume model, as described above, the physical occupancy of a body structure—the "volume", of a body structure—can be described under the assumption of the volume model.

There are different ways to define such a volume for structures. One option is to define a structure's volume as the set of all cubic cells whose interior geometrically coincide with the structure. Under this definition, there could be a cell having only a small portion of overlap with the structure, yet is still considered belonging to a structure's volume. Due to this, another option is described. This second option defines a structures' volume as the set of all cubic cells with at least 50% of its interior volume geometrically coincide with the structure. For each structure s, $V_s \subset D$ is defined as the set of coordinates corresponding to the cubic cells that are in volume of s.

All body structures in the model can be categorized as one of the two sets of structures. The first set is the planning target volume (PTV), $S_{PTV}$, which includes a set of different radiotherapy targets. The other set of structures includes the organs at risks (OAR), which is represented by $S_{OAR}$. These are the organs or tissues around the radiotherapy target that are inevitably exposed to radiation, and there are restrictions on the amount of radiation that these structures can be exposed to.

The IMRT beamlet model can also include a model for the beamlet, as described below.

Model for Beamlet

In model for the beamlet, it is assumed that the positioning of the beamlets are fixed. Let there be N beamlets. For the i-th beamlet, where $i \in \{1, 2, \ldots, N\}$, let $M_i$ be its $D_1 \times D_2 \times D_3$ radiation dose matrix per unit of the beam's intensity weight, in which the (j, k, l)-th element is the radiation dose (in a unit of certain radiation quantity, say Gray, or denoted by Gy for short) that the cubic volume (j, k, l) receives per unit of the beam's intensity. Furthermore, let $w \in \mathbb{R}_+^N$ be the vector of beamlet intensity weights, where its i-th element $w_i$ is the nonnegative intensity weight of the i-th beamlet. Note that $w \in \mathbb{R}_+$ is the set of all nonnegative real numbers. For a given beamlet intensity weight vector w, the total radiation dose is modeled as:

$$M(w) = \sum_{i=1}^{N} w_i M_i$$

In implementations where the optimization problem is an IMRT treatment problem, the received data may include data representing one or more dose-volume constraints, as described below.

Dose-Volume Constraints

For each structure $s \in S_{PTV}$ or $s \in S_{OAR}$, the dose-volume constraint is a pair of values, $(v_s, d_s)$, in which $v_s \in [0, 1]$ and $d_s \in \mathbb{R}_+$. Such pair of values is equivalent to the following statement:

$v_s$ of the entire volume of structure s receives at least $d_s$ Gray of radiation dose There can be multiple dose-volume constraints for each structure, and therefore, for each structure s with $r_s$ denoting the number of its dose-volume constraints, $(v_{s,i}, d_{s,i})$, denotes the i-th pair, where $i \in \{1, 2, \ldots, r_s\}$.

In implementations where the optimization problem is an IMRT treatment problem, the received data may include data representing an objective function to be minimized over beamlet intensity weights, as described below.

IMRT Beamlet Optimization Objective Function

The IMRT treatment objective function is based on a quantity of interest $\tilde{D}_{s,v}(w)$. Given a volume percentage $v \in [0, 1]$, and provided a structure s and beam intensity weight w, this quantity of interest $\tilde{D}_{s,v}(w) \in [0, 1]$ computes:

$\tilde{D}_{s,v}(w)$=the smallest dose (Gy) that v of the volume of s is at least receiving.

Which is equivalent to the v-quantile of the dose quantities of all the cubic cells in s, that is, $\tilde{D}_{s,v}(w) = v$ quantile of $\{M(w)_{x,y,z} : (x,y,z) \in V_s\}$ where $M(w)_{x,y,z}$ represents the (x, y, z)-th element of the total radiation dose matrix M(w), as defined above.

The objective of the IMRT beamlet optimization is to minimize the following objective function:

$$C(w) = \alpha \sum_{s \in S_{PTV}} \left(d_s - \tilde{D}_{s,v_s}(w)\right)^2 + \sum_{s \in S_{OAR}} \beta_s \sum_{i=1}^{r_s} \left(\max\{0, \tilde{D}_{s,v_{s,i}}(w) - d_{s,i}\}\right)^2$$

where $S_{PTV}$ represents a set of radiotherapy target body structures, $d_s$ represents a minimal amount of radiation dose to be received by structure s, $S_{OAR}$ represents a set of body structures that are at risk, $r_s$ represents the total number of dose-volume constraints for a structure s, $\alpha$ and $\beta_s$ are constants, $\tilde{D}_{s,v_s}(w)$ represents a smallest dose that $v_s$ of the volume of a respective body structure s is at least receiving, and w represents a vector of beamlet intensity weights where the i-th element $w_i$ of w represents a non-negative intensity weight of the i-th beamlet. The first term of the objective function is a total squared difference of the targeted treatment dosage and the actual dosage, summed over all PTVs. This represents the deviation from the prescription to the radiotherapy targets. The second term is the total squared amount of over-dosage on the organs at risk. This represents the amount of overdose on sensitive organs.

To apply some optimization techniques, e.g., those optimization techniques related to quantum computing, the IMRT beamlet optimization task can be discretized. For example, let $L \in \mathbb{N}$ represent the level of discretization. Each beamlet intensity weight $w_i$ can then be described by L binary variables $w_{i,1}, w_{i,2}, \ldots w_{i,L} \in \{0, 1\}$ such that $$\tilde{w}_i = \sum_{j=1}^{L} w_{i,j} 2^{j-1}.$$

In this way, $w_i$ can be any integer in the interval $[0, 2^L-1]$. Because the beamlet intensity weights $w_i$ are not freely varying integers and are fixed in a fixed range, a normalization can be applied to the radiation dose matrices M. Each matrix $M_i$ can be multiplied with a constant $\gamma \in \mathbb{R}^+$. Each individual radiation dose matrix is $\tilde{M} = \gamma M_i$, and the total radiation dose is $$M(w) = \sum_{i=1}^{N} w_i \tilde{M}_i = \sum_{i=1}^{N} w_i \gamma M_i$$

The choice of $\gamma$ takes the flexibility that the variables need into account. For example, in some implementations (e.g., those where it is assumed that $|S_{PTV}|=1$), $\gamma$ can be chosen such that $d_0 = \tilde{D}_{s,v_s}(w^*)$, where $w^* = (2^{L-1}, 2^{L-1})$. That is, $w^*$ is the instance when all variables are assigned the value $2^{L-1}$, which is close to the middle of the interval $[0, 2^L-1]$. This ensures that the variable w has the flexibility of moving away from the instance in which $d_0 = \tilde{D}_{s,v_s}(w)$. The binary representation of $w^*$ has $w_{i,j}^* = 1$ if $j=L$ and $w_{i,j}^* = 0$ otherwise. A single variable vector that stores all the $w_{i,j}$ is denoted by $\tilde{w}$ and can be defined by $\omega_{L(i-1)+j} = w_{i,j}$, $\forall i \in \{1, \ldots, N\}$, $j \in \{1, \ldots, L\}$.

The objective function C(w) can be redefined in terms of $\tilde{w}$ as $$C(\tilde{w}) = \alpha \sum_{s \in S_{PTV}} (d_s - \tilde{D}_{s,v_s}(F^{-1}(\tilde{w})))^2 + \sum_{s \in S_{OAR}} \beta_s \sum_{i=1}^{r_s} (\max\{0, \tilde{D}_{s,v_{s,i}}(F^{-1}(\tilde{w})) - d_{s,i}\})^2$$

where F represents a one-to-one mapping from w to $\tilde{w}$ defined by $F: \{0, \ldots, 2^L-1\}^N \to \{0,1\}^{N_B}$ with $N_B \equiv NL$ representing the length of the vector $\tilde{W}$.

Returning to FIG. 2, the system iteratively processes, until termination criteria are met, the received data representing the optimization problem to obtain data representing a solution to the optimization problem (step 204). For example, the system may iteratively process the received data until the difference between sequentially obtained outputs is smaller than a predetermined threshold. In some implementations an optimal choice of the predetermined threshold can be determined through evaluation of actual experimental runs and often varies case by case. In other implementations stopping criteria from other classical optimization heuristics, e.g., step-wise search, can be used.

For a first iteration, the system performs a classical search algorithm on an initial input (e.g., a randomly selected configuration of beamlet intensity weights) to determine a first solution to the optimization problem. The system then provides data representing the first solution to the optimization problem to a quantum computing resource. The data representing the first solution to the optimization problem can include a quadratic unconstrained binary optimization (QUBO) formulation of the optimization problem in a local region (defined as the locality within a given Hamming distance) around the first solution to the optimization problem, as described in more detail below. That is, the system can generate the QUBO formulation of the optimization problem in a local region around the first solution to the optimization problem. The system then obtains data representing a second solution to the optimization problem from the quantum computing resource, and provides the data representing the second solution to the optimization problem as input to a subsequent iteration.

In implementations where the optimization problem is an IMRT treatment problem, generating a QUBO formulation of the optimization problem in a local region around the first solution to the optimization problem includes generating a local second-order approximation of the IMRT objective function, as described below.

Local Second-Order Approximation of the Cost Function

Quantum annealing can solve binary optimization problems with objective functions that are quadratic polynomials of a set of binary variables. Since the IMRT objective function is not a quadratic polynomial (or even a low-order polynomial), in order to use quantum annealing, the IMRT objective function is approximated using second-order fitting. That is, the system determines a second-order function that fits all the first and second neighbors of a current location (determined by the classical search algorithm). The approximated IMRT objective function determines the objective to be optimized by the quantum computing resource. Determining a second-order function that fits all the first and second neighbors of a current location is as follows.

Given the current location $\tilde{w} = (\tilde{w}_1, \tilde{w}_2, \ldots, \tilde{w}_{N_B}) \in \{0, 1\}^{N_B}$, let M be an upper-triangular matrix of real values, i.e. $m_{i,j} \in \mathbb{R}$ $\forall i, j$:

$$M = \begin{bmatrix} m_{1,1} & m_{1,2} & m_{1,3} & \cdots & m_{1,N_B} \\ 0 & m_{2,2} & m_{2,3} & \cdots & m_{2,N_B} \\ \vdots & \vdots & \vdots & \vdots & \vdots \\ 0 & 0 & 0 & 0 & m_{N_B N_B} \end{bmatrix}$$

Let $u \in \{0, 1\}^{N_B}$ be a first or second neighbor of $\tilde{w}$ (or some other neighbour a predetermined distance away), that is, the Hamming distance of u and $\tilde{w}$ is $\leq 2$ (or less than or equal to another predetermined number. For larger Hamming distances, e.g., larger than 2, and the larger neighborhood within that distance, since there are $N_B (N_B+1)/2$ degrees of freedom in this model, $N_B (N_B+1)/2-1$ (excluding the center or original point that is included in the fitting) points in this neighborhood can be randomly selected, and the model can be fitted with those points. Including a larger neighborhood introduces flexibility and can overcome and prevent overfitting. For any such u, the equation $$u^T M u = C(u)$$

is imposed. There is a total of $$\binom{N_B}{1} + \binom{N_B}{2} = N_B + \frac{N_B(N_B-1)}{2} = \frac{N_B(N_B+1)}{2}$$

such equations. M is solved for by solving this systems of equations. The second-order approximation of the cost function C(.) at u is then:

$$u^T M u$$

It is noted that an upper-triangular matrix is sufficient, since $\forall u$ and for any matrix K, and considering the upper-triangular matrix M where $M_{i,j}=K_{i,j}+K_{j,i}$, $\forall i \leq j$, it can be shown that $u^T M u = u^T K u$.

Hamming Penalty in Local Quantum Annealing Search

In order to restrict the local quantum annealing search to find a candidate in the local "trust region" such that the second-order approximation is still accurate, the system can add a penalty term to the approximated cost function that is dependent on the Hamming distance of the candidate and the starting point. The Hamming penalty construction is described below.

Let $\tilde{w}^{(0)}=(\tilde{w}_1^{(0)}, \tilde{w}_2^{(0)}, \ldots, \tilde{w}_{N_B}^{(0)}) \in \{0,1\}^{N_B}$ be a starting point for an iteration, and let $\tilde{w}=(\tilde{w}_1, \tilde{w}_2, \ldots, \tilde{w}_{N_B}) \in \{0,1\}^{N_B}$ be a candidate point. The Hamming distance of $\tilde{w}^{(0)}$ and $\tilde{w}$ is:

$$d_H(\tilde{w}^{(0)}, \tilde{w}) \equiv (\tilde{w}^{(0)} - \tilde{w})^T(\tilde{w}^{(0)} - \tilde{w}) = \sum_{i=1}^{N_B}(\tilde{w}^{(0)} - \tilde{w}_i)^2 =$$

$$\sum_{i=1}^{N_B}(\tilde{w}_i^2 - 2\tilde{w}_i^{(0)}(\tilde{w}_i - \tilde{w}_i^{(0)2}),$$

and since $\tilde{w}_i \in \{0,1\}$, $\forall i$, as described above, $$d_H(\tilde{w}^{(0)}, \tilde{w}) = \sum_{i=1}^{N_B}(\tilde{w}_i - 2\tilde{w}_i^{(0)}\tilde{w}_i + \tilde{w}_i^{(0)2})$$

$$= \sum_{i=1}^{N_B}((1 - 2\tilde{w}_i^{(0)})\tilde{w}_i + \tilde{w}_i^{(0)2})$$

$$= \sum_{i=1}^{N_B}(1 - 2\tilde{w}_i^{(0)})\sum_{i=1}^{N_B}\tilde{w}_i^{(0)},$$

The Hamming distance therefore corresponds to a linear term. In implementations of the presently described Hamming penalty construction, there are two types of penalties—a scaled Hamming penalty and a scaled quadratic Hamming penalty.

The scaled Hamming penalty adds the following penalty term to the objective function:

$$P d_H(\tilde{w}^{(0)}, \tilde{w}),$$

where P>>0 is a large penalty constant.

The scaled quadratic Hamming penalty takes the form:

$$P d_H(\tilde{w}^{(0)}, \tilde{w})^2.$$

These penalties are at most second-order polynomials, and hence the resulting sum of them with the objective approximation is still quadratic.

Returning to FIG. 2, the system initiates an action based on the obtained data representing a solution to the optimization problem (step 206). For example, in implementations where the optimization problem is an IMRT treatment problem, the system can program a radiotherapy machine using the obtained beamlet intensity setting, or can operate the radiotherapy machine at the beamlet intensity setting as part of a IMRT treatment.

In some implementations the system may generate a user interface presentation based on the obtained data representing a solution to the optimization problem.

Example user interfaces generated by the system based on example process 200 in an IMRT treatment plan setting are shown in FIGS. 3-9.

Figure 3:
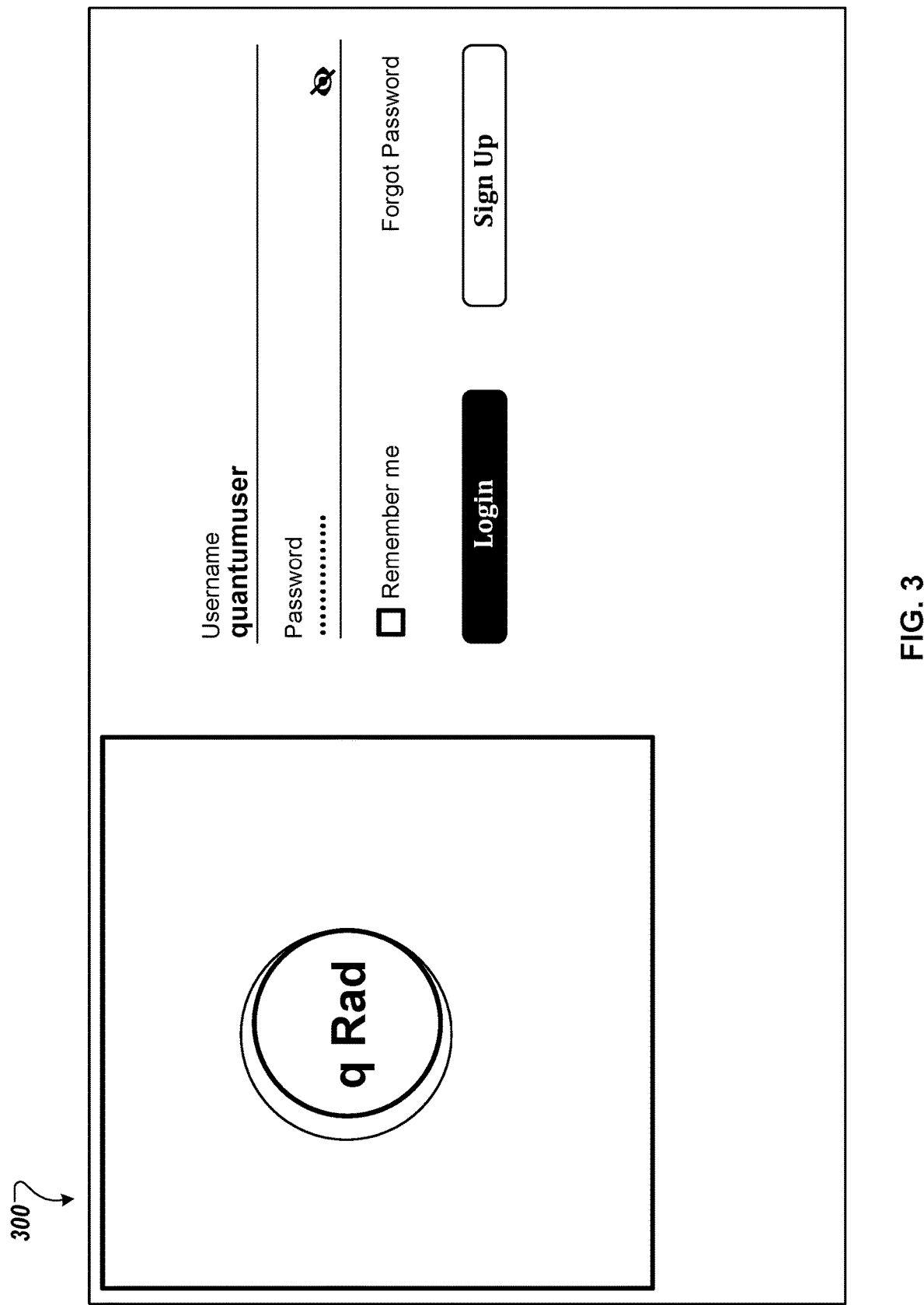
FIGS. 3-9 show example user interfaces.

FIG. 3 shows an example user interface presentation 300. The user interface presentation 300 enables a user, e.g., a medical professional, to log in to a system "q Rad" that generates solutions to IMRT treatment problems.

Figure 4:
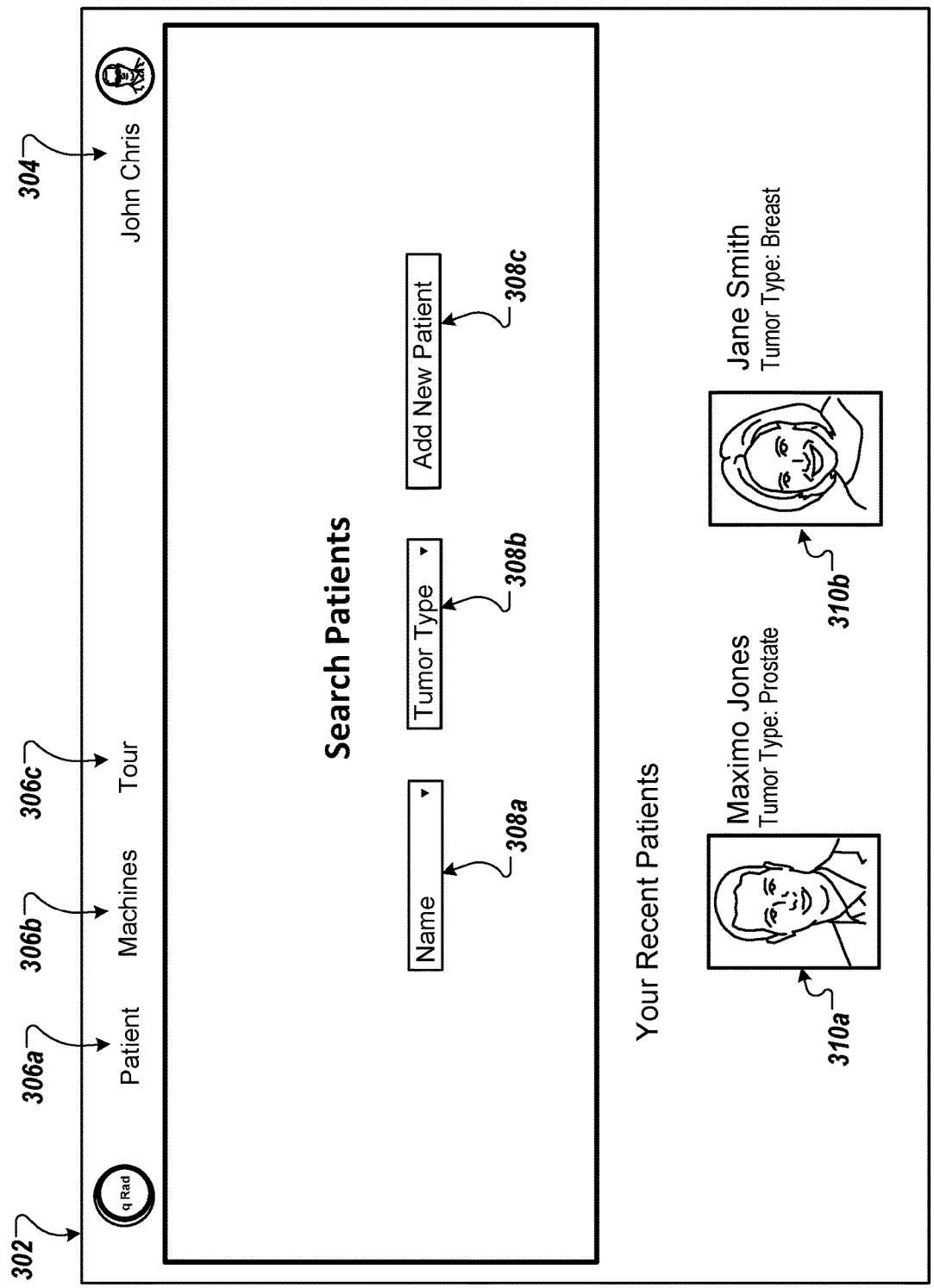

FIG. 4 shows an example user interface presentation 302. The user interface presentation 302 can be displayed when a user John Chris 304 has successfully logged in to the q Rad system using example user interface presentation 300. The user interface presentation 302 includes options 306a-b which, when selected by the user, causes the user interface presentation 302 to present different types of information.

For example, in response to the user selecting the patient option 306a, the user interface presentation 302 presents options 308a-c for searching a patient database or adding a new record to a patient database. Option 308a is a search field that enables a user to search the patient database based on patient name. In some implementations, user selection of option 308a can cause the user interface presentation 302 to display a drop down list of patients, e.g., in alphabetical order. In response to user selection of a patient included in the drop down list, a user interface presentation showing data related to the patient can be displayed, as described below with reference to FIG. 5. In some implementations, a user can input a patient name in option 308a. Input of a patient name can cause the user interface presentation 302 to display search results matching the input patient name, e.g., as a list of patients in alphabetical order. In response to user selection of a patient included in the search results, a user interface presentation showing data related to the patient can be displayed, as described below with reference to FIG. 5.

Option 308b is a search field that enables a user to search the patient database based on tumor type. In some implementations user selection of option 308b can cause the user interface presentation 302 to display a drop down list of tumor types, e.g., in alphabetical order. In response to user selection of a tumor type included in the drop down list, a user interface presentation showing patients diagnosed with the tumor type can be displayed. User selection of a patient with a tumor of the tumor type can cause the user interface presentation to display data related to the patient, as described below with reference to FIG. 5. In some implementations a user can input a tumor type in option 308a. Input of a tumor type can cause the user interface presentation 302 to display search results matching the input tumor type, e.g., as a list of tumor types in alphabetical order. In response to user selection of a tumor type included in the search results, a user interface presentation showing patients diagnosed with the tumor type can be displayed. User selection of a patient with a tumor of the tumor type can cause the user interface presentation to display data related to the patient, as described below with reference to FIG. 5.

Option 308c enables a user to add a new record to the patient database.

In some implementations, in response to the user selecting the patient option 306a, the user interface presentation 302 can present icons 310a-b representing patients recently viewed by the user, e.g., in a last login session or prior to selection of the patient option 306a. User selection of an icon 310a or 310b can cause the user interface presentation to display data related to the corresponding patient, as described below with reference to FIG. 5.

In response to the user selecting the machine option 306b the user can be presented with an an overview of available machines.

Figure 5:
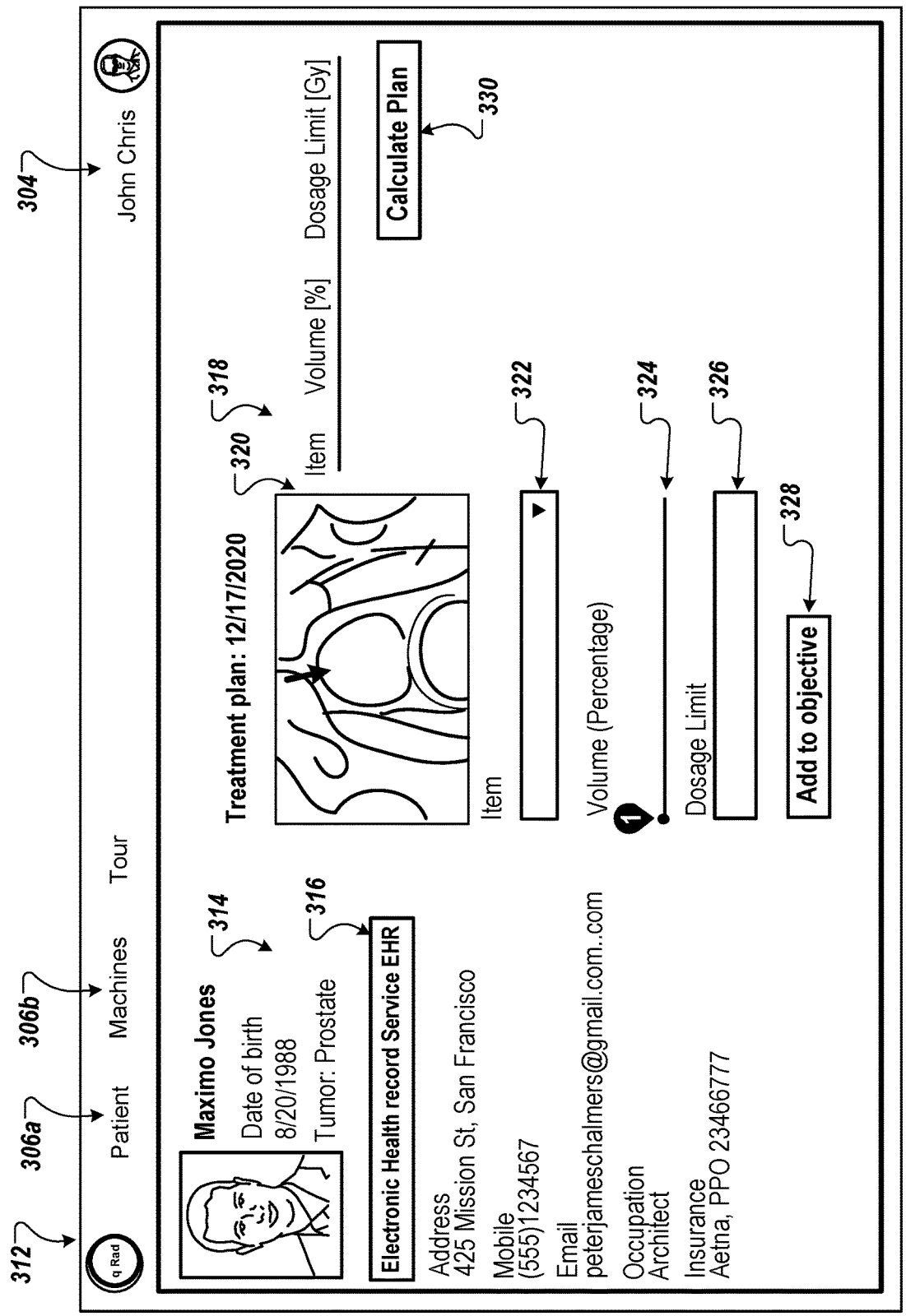

FIG. 5 shows an example user interface presentation 312. The user interface presentation 312 shows data relating to a patient undergoing IMRT, e.g., as selected by a user through user interface 302. A first portion 314 of the user interface presentation 312 displays personal information for the patient, e.g., patient name, date of birth, contact details, address, and insurance provider. In some implementations the first portion 314 can include an option 316 which, when selected, opens an electronic health record for the patient.

A second portion 318 of the user interface presentation 312 enables the user to interact with the q-rad system to calculate an optimal IMRT treatment plan for the patient. For example, the second portion 318 of the user interface presentation 312 includes an image, e.g., a most recent image, of the patient's tumor. In addition, the second portion 318 of the user interface presentation 312 includes options 322-328 for inputting data including tumour type, location, and volume-dose constraints, e.g., data specifying an objective function to be minimized (or maximized) with respect to a set of parameters and data representing constraints for the minimization (or optimization) as described at step 202 with reference to FIG. 2. For example, option 322 enables the user to input a target body structure or body structure at risk from the treatment. Option 324 enables the user to select a volume of the body structure input at option 322, e.g., as a percentage. Option 326 enables the user to select a dosage limit for the volume of the body structure. After the user completes options 322, 324 and 326, the user can select option 328 to add the volume-dose constraint to the IMRT objective function.

Figure 6:
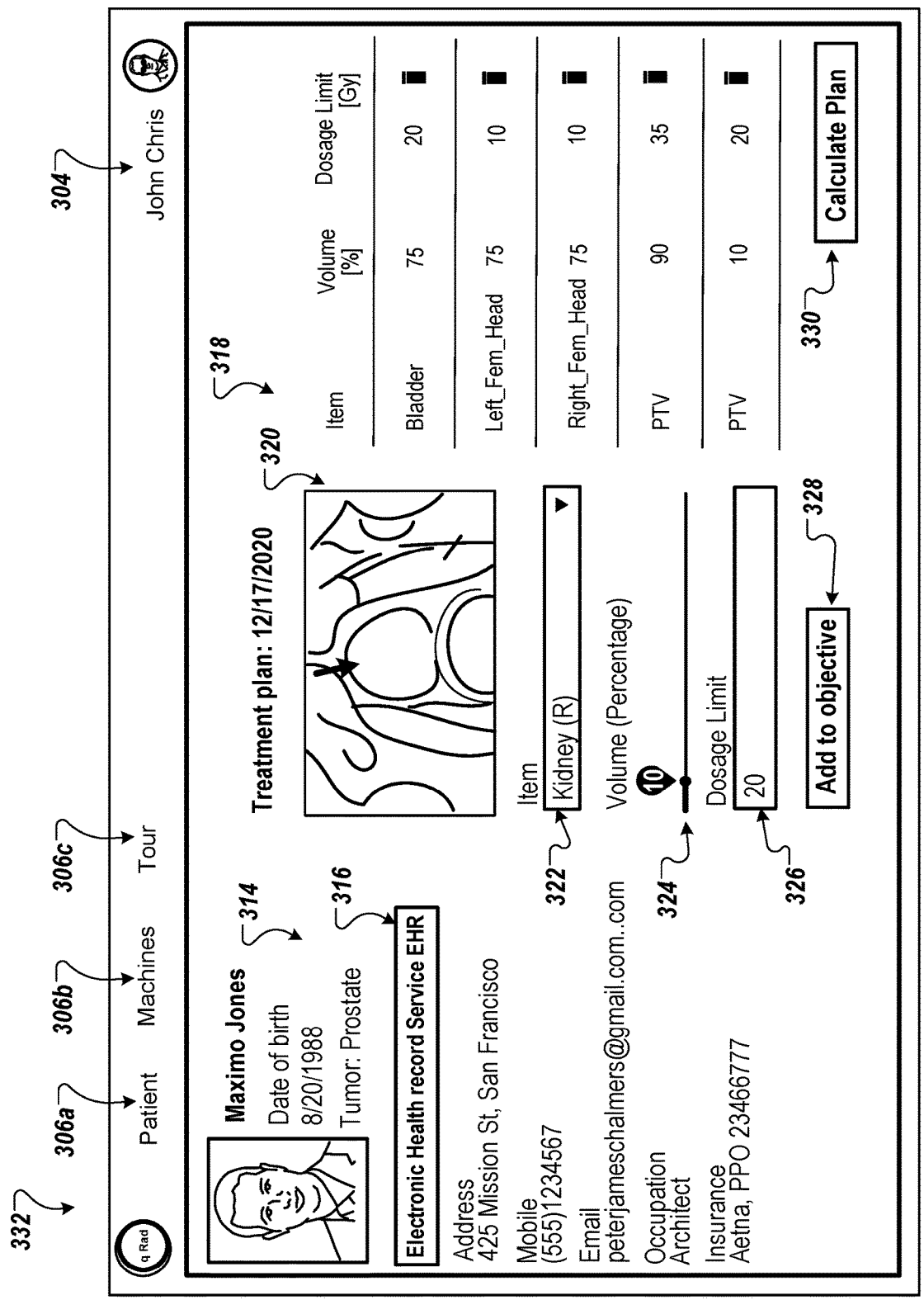

FIG. 6 shows an example user interface presentation 332. The user interface presentation 332 shows example user interface presentation 312 after the user has entered multiple volume-dose constraints. For example, the user has entered the right kidney in option 322, specified a volume of 10% in option 324, and entered a dosage limit of 20Gy in option 326. The user can select option 328 to add this volume-dose constraint to the IMRT objective function. After adding a volume-dose constraint to the IMRT objective function, a summary of the volume-dose constraint is displayed on the right hand side of portion 318. In this example, the user has already entered five volume-dose constraints for the patient's bladder, left femoral head, right femoral head, and planning target volumes (PTV). Added volume-dose constraints can be deleted by selecting the trash options next to the displayed volume-dose constraints.

When a user has entered all required volume-dose constraints, the user can request a corresponding IMRT treatment plan by selecting the calculate plan option 330. Selection of the calculate plan option 330 causes the system to execute step 204 of example process 200 described with reference to FIG. 2 using the received input data.

Figure 7:
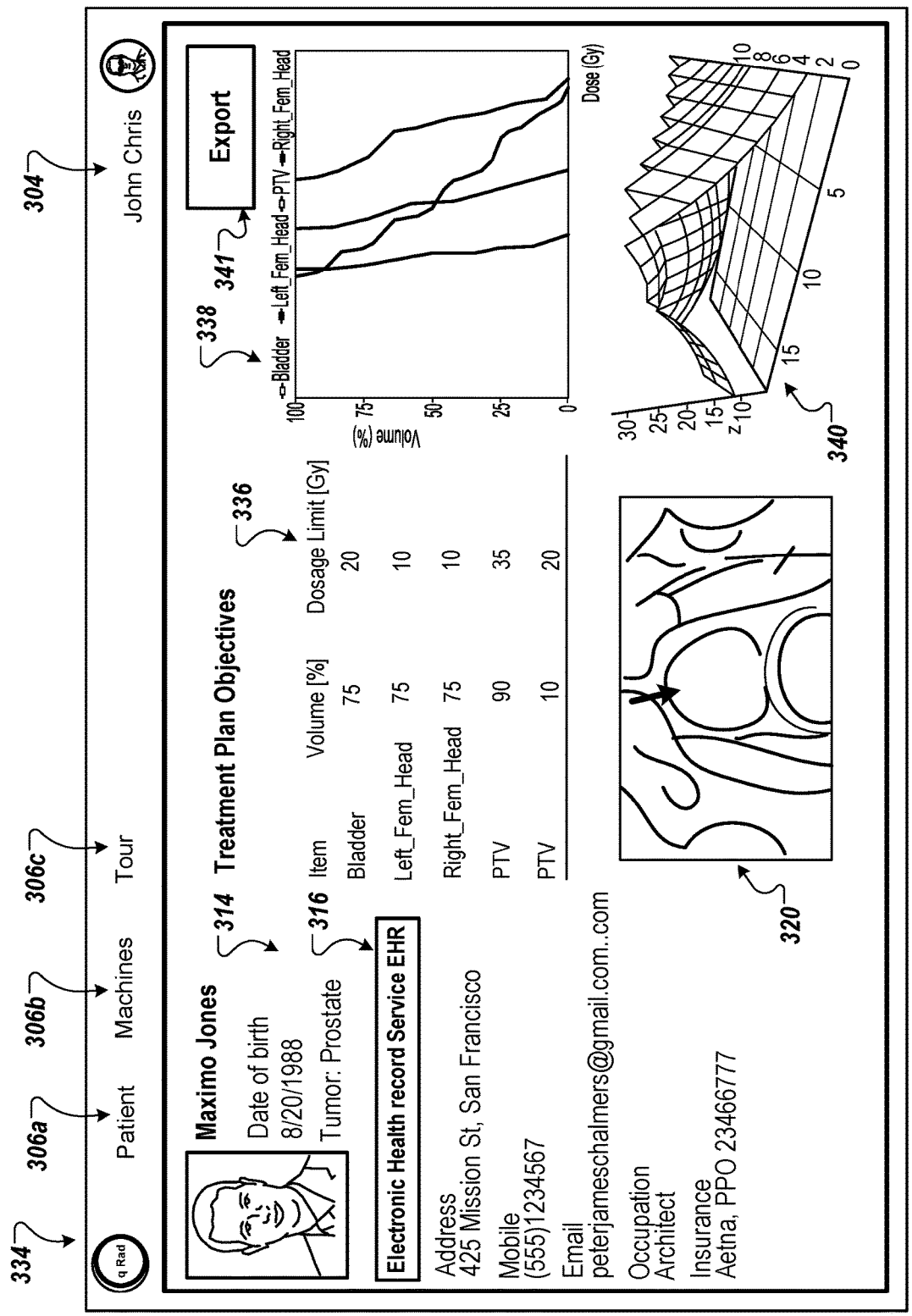

FIG. 7 shows an example user interface presentation 334. The user interface presentation 334 shows example user interface presentation 332 after the user inputs volume-dose constraints and other information to define a corresponding IMRT objective function and selects the calculate plan option 330. The user interface presentation 334 shows information relating to a corresponding IMRT treatment plan. For example, the user interface presentation 334 includes a summary 336 of the volume-dose constraints input by the user in example user interface presentation 332 and the image of the tumor shown in example user interface presentation 332.

The user interface presentation 334 further includes graphs 338 and 340 that enable the user to visualize the solution to the IMRT treatment plan problem, e.g., the generated treatment plan. Graph 338 shows a dose-volume histogram for each input body structure. Graph 340 shows a three-dimensional representations of the generated treatment plan, where the surface would be coloured according to Gy intensity. The user can export the generated plan by selection of the export option 341. For example, the user can export the generated plan as machine instructions which can be directly transmitted to a IMRT machine to program the machine to execute the generated treatment plan.

Figure 8:
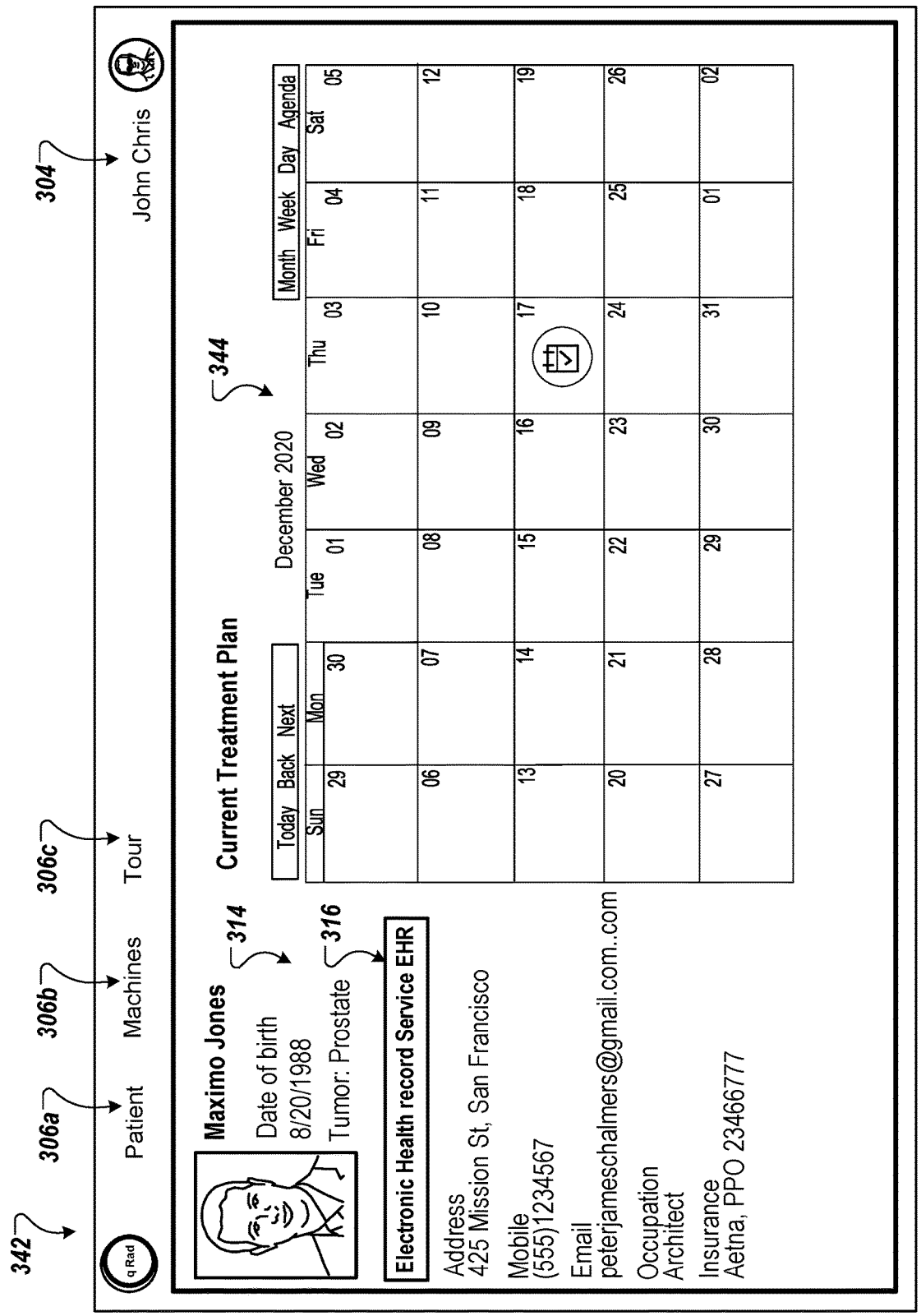

FIG. 8 shows an example user interface presentation 342. The user interface presentation 342 displays a calendar view 344 and enables a user to view the dates and details of previously generated treatment plans, and to add a new upcoming calculated treatment plans, e.g., the treatment plan calculated and displayed in user interfaces 332, 334. A user can select a previously generated plan and view or adjust the plan. For example, a user may select a planned treatment and adjust values associated with the treatment plan to update the treatment plan or calculate a new plan. Selection of a previously generated plan can cause the user interface presentation 342 to display a presentation similar to user interface presentation 334 or 332, through which the user can select and adjust previously entered volume-dose constraints.

Figure 9:
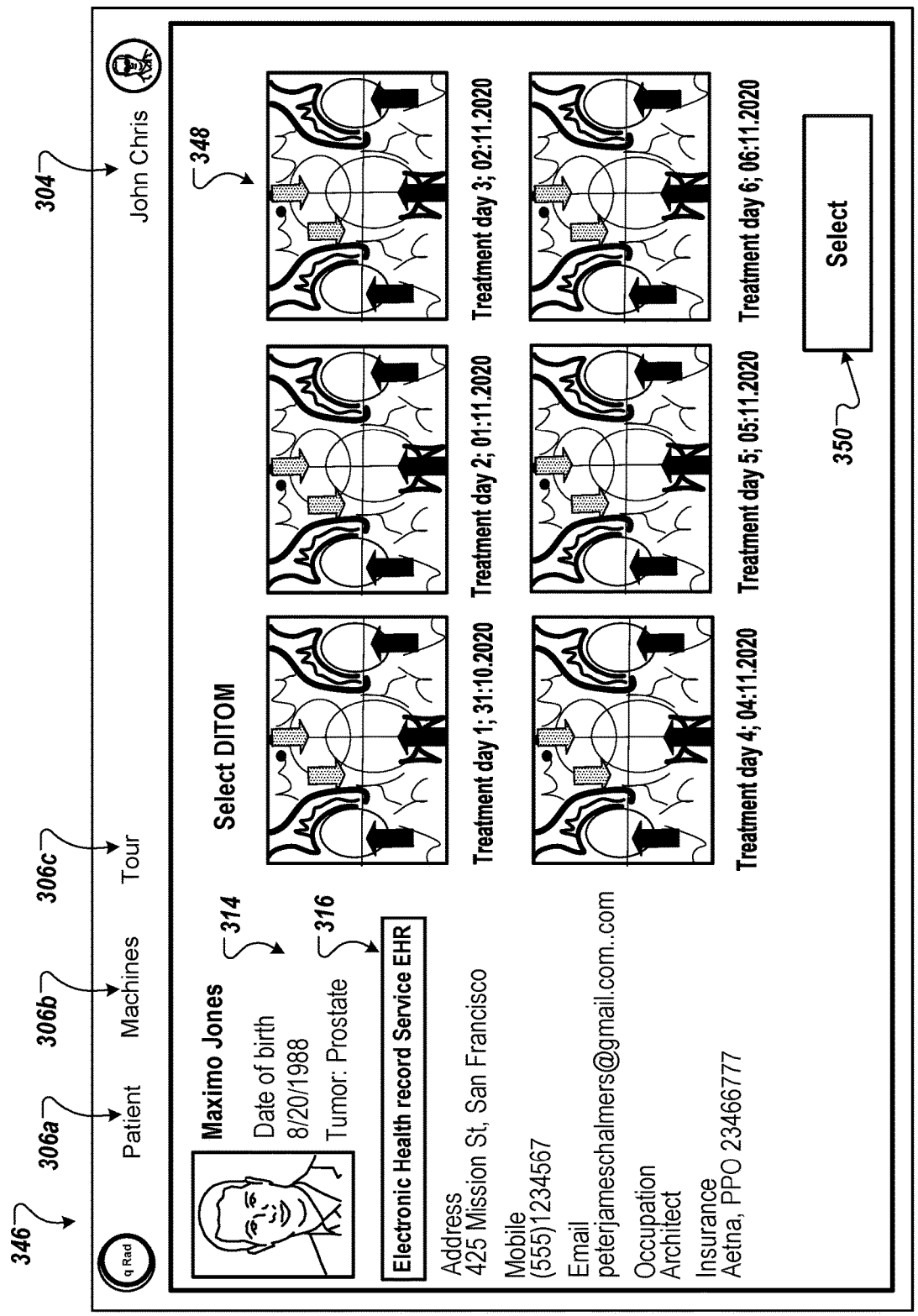

FIG. 9 shows an example user interface presentation 346. The user interface presentation 346 displays images 348 related to calculated treatment plans for different days, and enables a user to compare the different treatments and in some cases the patient's response to the treatments. The user can highlight a particular image and select the select option 350 to view a treatment plan performed on the date of the image, e.g., selection of the select option 350 can cause the user interface presentation 346 to display a presentation similar to user interface presentation 334 or 332.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computing device" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible. The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons, or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators. Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
   receiving data relating to an optimization problem, wherein the optimization problem comprises an objective function to be optimized over multiple problem parameters;
   iteratively processing, until termination criteria are met, the received data relating to the optimization problem to obtain data representing a solution to the optimization problem, comprising, for each iteration:
   performing a classical search algorithm on an input for the iteration to determine a first solution to the optimization problem;
   providing data relating to the first solution to the optimization problem to a quantum computing resource, wherein the data relating to the first solution to the optimization problem comprises a quadratic unconstrained binary optimization (QUBO) formulation of the optimization problem in a local region around the first solution to the optimization problem;
   generating the quadratic unconstrained binary optimization (QUBO) formulation of the optimization problem in the local region around the first solution to the optimization problem, comprising:
   selecting a discretization for the optimization problem;
   applying the discretization to the optimization problem to obtain discretized values of the multiple problem parameters, wherein each discretized value comprises a respective binary sequence; and
   determining a binary sequence corresponding to a discretization of the first solution to the optimization task;
   obtaining data relating to a second solution to the optimization problem from the quantum computing resource; and
   providing the data relating to the second solution to the optimization problem as input to a subsequent iteration;
   receiving solution data from the processing; and
   initiating an action based on the solution data.

2. The method of claim 1, wherein the local region around the first solution to the optimization problem comprises multiple discretized values of the multiple problem parameters, wherein:
   a Hamming distance between each discretized value and a binary sequence representation of the first solution is at most 2.

3. The method of claim 1, wherein selecting the discretization for the optimization problem comprises selecting a normalization factor to position the discretization of the first solution to the optimization task in a centre of a corresponding discretization interval.

4. The method of claim 1, wherein generating the quadratic unconstrained binary optimization (QUBO) formulation of the optimization problem in the local region around the first solution to the optimization problem further comprises:
   determining a set of second bit sequences, wherein a Hamming distance of a first bit sequence relating to representing the first solution and each second bit sequence is at most 2;
   generating a system of equations, comprising, for each second bit sequence in the set of second bit sequences:
   determining a product of i) a transposed vector form of the second bit sequence, ii) a matrix relating to total radiation dose, and iii) a vector form of the second bit sequence; and
   setting the determined product as equal to an objective function for the optimization problem evaluated at the second bit sequence; and
   solving the system of equations to determine entries of the matrix relating to total radiation dose.

5. The method of claim 4, wherein the matrix comprises an upper triangular matrix.

6. The method of claim 4, wherein the first bit sequence and each second bit sequence have a length equal to a number of optimization problem parameters.

7. The method of claim 4, wherein the generated system of equations comprises $$\frac{N_B(N_B+1)}{2}$$

equations, wherein $N_B$ relates to a number of optimization problem parameters.

8. The method of claim 1, wherein the QUBO formulation of the optimization problem in the local region around the first solution to the optimization problem comprises a scaled Hamming penalty.

9. The method of claim 1, wherein the QUBO formulation of the optimization problem in the local region around the first solution to the optimization problem comprises a scaled quadratic Hamming penalty.

10. The method of claim 1, wherein the optimization problem comprises an intensity-modulated radiation therapy (IMRT) treatment problem.

11. The method of claim 10, wherein the IMRT treatment problem comprises an objective function to be minimized, wherein the objective function comprises a linear combination of two terms, a first term relating to differences between i) a minimal amount of radiation dose to be received by a target body structure and ii) a smallest dose a volume of the target body structure receives, and a second term relating to an amount that the minimal amount of radiation dose to be received by a body structure at risk exceeds a smallest dose a volume of the body structure at risk receives.

12. The method of claim 11, wherein the objective function is given by $$C(w) = \alpha \sum_{s \in S_{PTV}} (d_s - \tilde{D}_{s,v_s}(w))^2 + \sum_{s \in S_{OAR}} \beta_s \sum_{i=1}^{r_s} (\max\{0, \tilde{D}_{s,v_{s,i}}(w) - d_{s,i}\})^2$$

where SPTV represents a set of radiotherapy target body structures, $d_s$ relates to the minimal amount of radiation dose to be received by structure s, SaAR relates to a set of body structures that are at risk, $r_s$ relates to a total number of dose-volume constraints for a structures s, $\alpha$ and $\beta_s$ are constants, $D_{s,v_s}(w)$ relates to a smallest dose that vs of the volume of a respective body structures is at least receiving, and w relates to a vector of beamlet intensity weights where the i-th element $W_i$ of w relates to a non-negative intensity weight of the i-th beamlet.

13. The method of claim 10, wherein the IMRT treatment problem comprises one or more dose-volume constraints, wherein each dose-volume constraint comprises a pair of values $(v_s, d_s)$ that specify a minimal amount of the radiation dose $d_s$ to be received by a total volume $V_s$ of a respective body structure s.

14. The method of claim 10, wherein the received data comprises patient specific data comprising a set of radiotherapy targets and a set of organs at risk.

15. The method of claim 10, wherein the solution to the optimization problem comprises a beamlet intensity setting for the IMRT treatment problem.

16. The method of claim 15, wherein initiating an action based on the obtained data relating to a solution to the optimization problem comprises one or more of: programming a radiotherapy machine using the beamlet intensity setting, or operating the radiotherapy machine at the beamlet intensity setting.

17. A system comprising:
one or more computers; and
one or more computer-readable media coupled to the one or more computers having instructions stored thereon which, when executed by the one or more computers, cause the one or more computers to perform operations comprising:
receiving data relating to an optimization problem, wherein the optimization problem comprises an objective function to be optimized over multiple problem parameters;
iteratively processing, until termination criteria are met, the received data relating to the optimization problem to obtain data relating to a solution to the optimization problem, comprising, for each iteration:
performing a classical search algorithm on an input for the iteration to determine a first solution to the optimization problem;
providing data relating to the first solution to the optimization problem to a quantum computing resource, wherein the data relating to the first solution to the optimization problem comprises a quadratic unconstrained binary optimization (QUBO) formulation of the optimization problem in a local region around the first solution to the optimization problem;
generating the quadratic unconstrained binary optimization (QUBO) formulation of the optimization problem in a local region around the first solution to the optimization problem, comprising:
selecting a discretization for the optimization problem;
applying the discretization to the optimization problem to obtain discretized values of the multiple problem parameters, wherein each discretized value comprises a respective binary sequence; and
determining a binary sequence corresponding to a discretization of the first solution to the optimization task;
obtaining data relating to a second solution to the optimization problem from the quantum computing resource; and
providing the data relating to the second solution to the optimization problem as input to a subsequent iteration;
receiving solution data from the processing; and
initiating an action based on the solution data.

18. One or more non-transitory computer storage media encoded with a computer program, the program comprising instructions that when executed by a data processing apparatus cause the data processing apparatus to perform operations comprising:
receiving data relating to an optimization problem, wherein the optimization problem comprises an objective function to be optimized over multiple problem parameters;
iteratively processing, until termination criteria are met, the received data relating to the optimization problem to obtain data relating to a solution to the optimization problem, comprising, for each iteration:
performing a classical search algorithm on an input for the iteration to determine a first solution to the optimization problem;
providing data relating to the first solution to the optimization problem to a quantum computing resource, wherein the data relating to the first solution to the optimization problem comprises a quadratic unconstrained binary optimization (QUBO) formulation of the optimization problem in a local region around the first solution to the optimization problem;

generating the quadratic unconstrained binary optimization (QUBO) formulation of the optimization problem in a local region around the first solution to the optimization problem, comprising:

selecting a discretization for the optimization problem;

applying the discretization to the optimization problem to obtain discretized values of the multiple problem parameters, wherein each discretized value comprises a respective binary sequence; and determining a binary sequence corresponding to a discretization of the first solution to the optimization task;

obtaining data relating to a second solution to the optimization problem from the quantum computing resource; and providing the data relating to the second solution to the optimization problem as input to a subsequent iteration;

receiving solution data from the processing; and initiating an action based on the solution data.

* * * * *